United States Patent [19]

Rittenburg et al.

[11] 4,215,108
[45] Jul. 29, 1980

[54] LOBSTER GAFFKEMIA VACCINE

[75] Inventors: James H. Rittenburg, Stillwater; Robert C. Bayer, Orono, both of Me.

[73] Assignee: Research Corporation, New York, N.Y.

[21] Appl. No.: 40,296

[22] Filed: May 18, 1979

Related U.S. Application Data

[63] Continuation of Ser. No. 969,078, Dec. 13, 1978, abandoned.

[51] Int. Cl.$^2$ ............................................. A61K 39/02
[52] U.S. Cl. ........................................................ 424/92
[58] Field of Search ......................................... 424/92

[56] References Cited

PUBLICATIONS

Stewart Marine Fisheries Review 37(56):20–24 May, Jun. 1975, Gaffkemia, The Fatal Infection of Lobsters (Genus Homarus) Caused by Aerococcus viridans Var. Homari: A Review.
Stewart et al., J. Fish. Res. Board. Can. 31:1887–1892 (1974), Comparison of Various Vaccines for Inducing Resistance in the Lobster Homarus americanus to the Bacterial Infection Gaffkemia.
Stewart et al., J. Fish. Res. Board Can 31(12):1873–1879(1974), Effectiveness of Vancomycin Against Gaffkemia the Bacterial Disease of Lobsters (Genus Homarus).
Schapiro American Zoologist 15:13–19 (1975), Immunity in Decapod Crustaceans.
Schapiro et al., Aquaculture 3(1974):403–408, Gaffkemia in the California Spiny Lobster, Infection and Immunization.
Schapiro et al., Active Immunity to Gaffkemia in Lobsters (1976), 4 pp., World Mariculture Society Workshop on 145–147 (1976).
Steen Bergen et al., Gaffkemia in California, Spiny Lobsters (1976), 6 pp., World Mariculture Society Workshop, pp. 134–143 (1976).
Mori et al., J. Fish. Res. Board. Can 35 (1978), 1504–1507, The Hemolymph Bactericidin of American Lobster (Homarus americanus).
Mori et al., J. Invert. Pathol 32(2):171–176 (1978), Natural and Induced Bactericidal Activites of the Hepatopancreas in the American Lobster (Homarus americanus).

Primary Examiner—Shep K. Rose
Attorney, Agent, or Firm—Haight & Huard

[57] ABSTRACT

A method for preparing a vaccine suitable for use in protecting lobsters against gaffkemia, which comprises:
(a) culturing a logarithmic growth phase of the bacteria Aerococcus viridans (Var. Homari) in a suitable growth medium containing sources of assimilable complete nutrients for said bacteria;
(b) adding a sublethal, replication-inhibiting amount of an antibiotic effective against said bacteria to said culture and incubating the resultant admixture for a period for time sufficient to accumulate antigens therein protective against gaffkemia infections; and
(c) recovering said protective antigens to form a vaccine containing an immunologically effective amount of said antigens free of said living bacteria and substantially free of in vivo effective amounts of said antibiotic.

10 Claims, No Drawings

LOBSTER GAFFKEMIA VACCINE

This is a continuation of application Ser. No. 969,078 filed Dec. 13, 1978, now abandoned.

DESCRIPTION OF THE INVENTION

1. Technical Field of the Invention

This invention relates to a method for preparing an effective vaccine to protect lobsters from gaffkemia, to the vaccine so produced and to a method for immunizing lobsters against gaffkemia with said vaccine.

Gaffkemia or "red tail" is a usually fatal infection of lobsters of the genus Homarus which is caused by the microorganism *Aerococcus viridans* (var.) *homari* widely occurring in nature. While the almost uniformly fatal consequence of this disease is limited in nature to those lobsters so afflicted, these animals become carriers of the disease in the commercial harvesting of lobsters, causing severe economic loss when epidemics of this disease periodically break out within lobster holding units. In the State of Maine alone, over two million lobsters are held in pounds each year and losses due to gaffkemia of 15% are common in some years. Gaffkemia is not only a problem affecting the lobster industries of the U.S. and Canada, but also affects other lobster species of commercial interest in the United Kingdom, Norway, Australia, New Zealand and South Africa.

Reviews of the current state of the art with respect to this disease have been published by Stewart et al. in Marine Fisheries Review 37 (5–6): 20–24 (MFR Paper 1142, May–June 1975); J. Fish. Res. Board Can. 31 (12): 1873–1879 (1974); and J. Fish. Res. Board Can. 31 (12): 1887–1892 (1974), the contents of which are incorporated by reference herein.

BACKGROUND ART

In spite of these extensive studies, resistance of lobsters to the Aerococcus has been obtained only rarely. In one experiment reported by Stewart, filter sterilized serum from heavily infected lobsters was injected into healthy animals in massive amounts; this had no adverse effect but apparently was not studied to determine if any immunity was conferred. The lack of infectivity is, by the same author, indicated as possibly attributable to a lack of virulence or a change in virulence of the pathogen. A limited degree of resistance has been observed upon injection of vaccines prepared from formalin-killed cells of a virulent strains grown both in vitro and in vivo, but only a low level of protection was achieved.

The best protection heretofore obtained has been achieved by injecting the lobsters with an initial dose of vancomycin, followed by injection of live pathogen cells 24 hours later. However, this method has a serious drawback in that the amounts of vancomycin used are over a thousandfold greater than in the vaccine of the present invention and the resultant lobster meat is accordingly contaminated with residual amounts of the antibiotic.

DISCLOSURE OF THE INVENTION

Accordingly, it is a general object of the present invention to provide a method for preparing an effective vaccine against lobster gaffkemia.

Another object of the present invention is to provide such a vaccine, particularly one which is free of virulent *Aerococcus viridans* (var.) *homari* and especially one which is substantially free of residual amounts of antibiotics so that the harvested lobster is not contaminated thereby.

A further object of the present invention is to provide a method for effectively preventing the spreading of gaffkemia in lobster holding pounds.

Upon study of the specification and appended claims, further objects, features and advantages of the present invention will become more fully apparent to those skilled in the art to which this invention pertains.

BEST MODE FOR CARRYING OUT THE INVENTION

Briefly, the above and other objects, features and advantages of the present invention are attained in one aspect thereof by providing a method for preparing a vaccine suitable for use in protecting lobsters against gaffkemia, which comprises:

(a) culturing a logarithmic growth phase of the bacteria *Aerococcus viridans* (var. *homari*) in a suitable growth medium containing sources of assimilable complete nutrients for said bacteria;

(b) adding a sublethal, replication-inhibiting amount of an antibiotic effective against said bacteria to said culture and incubating the resultant admixture for a period for time sufficient to accumulate antigens therein protective against gaffkemia infections; and (c) recovering said protective antigens to form a vaccine containing an immunologically effective amount of said antigens free of said living bacteria and substantially free of in vivo effective amounts of said antibiotic.

*Aerococcus viridans* (var.) *homari* is readily isolatable from lobsters in nature and its availability is commonly known; the particular strain employed is not critical and forms no part of the present invention. According to a first aspect of the present invention, the Aerococcus is cultivated in vitro in a suitable growth medium such as trypicase soy broth by techniques well known in the art; the present inventors have found that especially good results can be obtained when the growth medium containing a complete source of assimilable nutrients is supplemented with a growth-promoting amount, e.g. 1–15% by volume, of a nutrient serum such as fetal calf serum or crustacean serum, e.g. crab serum. The only requirement of the nutrient medium is that it be capable of supporting growth of the Aerococcus. The culture is incubated under cellular growth conditions in a sterile container and at a suitable incubation temperature, e.g. of about 30°–42° C., preferably about 35°–37° C.

After logarithmic growth has been achieved by several serial transfers, a sublethal dose of an antibiotic such as vancomycin is added in amount sufficient to inhibit further replication. Other suitable antibiotics which similarly inhibit replication of the Aerococcus can also be employed; such agents are well known in the art and include but are not limited to antibiotics of the ristocetin, penicillin, tetracycline, ampicillin and chloromycetin families.

While illustrated herein principally with reference to the Aerococcus, the method of the present invention is in principle applicable to many other types of bacteria which exhibit a similar inhibitory reaction upon treatment with sublethal dosages of effective antibiotics, e.g. streptococcus, staphylococcus, etc. which cause infections in species other than the lobster. For example, using the process for producing vaccines to streptococcus and staphylococcus, it may well be possible to increase the number of antigenic determinants of the immunogenic substance. Since other gram positive cocci have a cell wall similar to that of *A. viridans,* their immunogenic capacity may be increased by treatment with a cell wall replication inhibiting substance in a manner similar to the use of vancomycin with *A. viridans.* Possibly incomplete cell wall synthesis may leave certain antigenic determinant sites exposed, which normally are hidden by complete cell wall synthesis. While not wishing to be bound by any theory of the invention, it is presently believed that a toxoid of some type, possibly a cell wall precursor, is released by the cells into the medium rather than incorporated as usual into the cell wall; these precursors could serve as an active immunogen. The required dosage can be readily determined by a few simple serial dilution Minimum Inhibitory Concentration (MIC) assays. Generally, suitable dosages for the presently preferred antibiotic vancomycin are in the range of about 1–3 mg/l.

The culture is incubated for a period of time sufficient to accumulate antigenic material, generally requiring 4 to 24, commonly about 12 hours at about 37° C. although lower or higher conventional incubation temperatures can be used. Production of the antigenic material can if desired be monitored by spectrophotometric methods, e.g. by monitoring at 420 nm against a culture medium blank (such as trypticase soy broth), an optical density of 0.05–0.15, generally about 0.1, indicates the appropriate time for the addition of the antibiotic.

After accumulation of sufficient antigenic material, the Aerococcus is then killed, e.g. by exposure to short wave ultraviolet radiation at a frequency of about 254 nm or by autoclaving, e.g. at about 121° C. under a pressure of about 15 psi for 10–20 minutes. The use of a logarithmic growth phase, continuing culturing after the addition of the antibiotic and 100% freedom from living Aerococcus are all essential to obtaining the desired vaccine product.

Since vancomycin is most effective during the stages of most rapid bacterial replication, the prior art results of injecting lobsters with vancomycin followed by the live pathogen a day later have been speculated to be due to a reduction in the rate of replication coupled with an immediate build-up of mucopeptide precursors which could be complexed with vancomycin; while not wishing to be bound by any theory of the invention, it is presently believed that these may comprise at least a portion of the active antigen materials in the vaccine of the present invention. Nonetheless, this has been done in the past only in vivo and the amounts of vancomycin used have been at least one milligram per kilogram of body weight, far greater than the residual amounts present in the subject vaccine. Furthermore, none of the prior art employs in vitro cultivation of this organism in the presence of a serum supplement of any kind.

It will be apparent to those skilled in the art to which this invention pertains that antibiotics other than vancomycin can be used to inhibit replication of the bacteria, although vancomycin at present is preferred due to its good activity against the Aerococcus. Starting with the logarithmic growth stage, the antibiotic inhibits replication while not interferring with the production of suitable antigenic material. While it is presently believed that the antigen itself is particulate, there is a possibility that some or even all of the antigen could be a soluble product; accordingly, the presently preferred final vaccine employed is a resuspension of killed cells in the original culture medium.

The presently preferred gaffkemia antigen recovery method involves separating the resultant cells from the supernatant prior to sterilization and recombination of the sterilized cells with the supernatant to form the vaccine. The supernatant can be collected by centrifugation or filtration and generally has a protein content of 0.05–0.1 mg per ml as determined by the Folin-phenol method of Lowry et al.

Separation prior to sterilization is practiced mainly to facilitate sterilization with readily available UV equipment generally on hand in the laboratory, but in principle there appears to be no reason why a thin layer of culture media could not be passed between two quartz plates for UV sterilization without prior cell separation. As it is not presently known whether the antigenically active material is present chiefly in the centrifuged pellet or residual supernatant, when the particulate material is separated for sterilization it is then re-combined to form the final vaccine.

Sterilization is preferably effected using exposure to short wave ultraviolet radiation since this causes less protein denaturation, but other means of sterilization known in the prior art can likewise be employed, e.g. heat inactivation by autoclaving and probably gamma-radiation or formalin inactivation. Due to the high virulence of the organism in the lobster, it is, however, essential that no virulent bacteria be present in the vaccine product; in accordance with the present invention, it is essential that the residual amounts of antibiotic in the vaccine as actually administered must be nil. While the inventors do not presently have a complete theoretical explanation for the success of this vaccine, one outstanding difference between that and those known in the prior art is that the vaccine of the present invention clearly works effectively without the necessity of injecting prohibitively high amounts of vancomycin into the lobsters. Residual amounts are less than a microgram per animal, and undetectable by present-day analytical techniques.

For the preparation of vaccines suitable for immunizing lobsters against gaffkemia or for the preparation of diagnostic antibodies in laboratory animals, conventional vaccine preparation techniques can be used. If desired, a non-antigenic adjuvant, e.g. alum, Freund's adjuvant, saponin, a quaternary ammonium surfactant, an alkyl amine, etc. can be mixed with the vaccine in a suitable pharmaceutically acceptable carrier and the resultant mixture sterilized.

Generally, the vaccine of this invention is dispensed in unit dosage form comprising 100–5,000 mg. of a pharmaceutical carrier per each unit dosage and the amount of active agent of the invention per unit dosage is about 1 to 50 mg., preferably about 4 to 12 mg. The vaccine is substantially free of residual antibiotic, and generally contains less than 0.0005 and no more than 0.002 mg. of residual antibiotic per 0.5 ml. unit dosage.

The vaccine of this invention is generally administered to lobsters by injection at the time of transferring the animals from holding crates to holding ponds for long term storage. An effective dosage of the vaccine administered intramuscularly generally comprises about 1 to 50, preferably 10 to 20 and especially about 7 mg/kg, together with 10–5,000 mg. of a pharmaceutically acceptable carrier. The dose can be administered singly or booster shots can be added if desired. Alternatively, the immersion method of Ament et al. U.S. Pat. No. 4,009,259, the contents of which are incorporated by reference herein, might be employed.

It will be appreciated that the actual preferred amounts of the vaccine used will vary according to the particular compositions formulated, the mode of application, and the particular situs and organism being treated. Optimal application rates for a given set of conditions can be ascertained by those skilled in the art using conventional dosage determination tests in view of the above guidelines.

Prior art antibiotic treatment with vancomycin has been effective; however, due to present drug laws, commercial treatment with this drug is not possible. Various vaccines have also been tried. A low degree of protection was achieved using a formalin killed preparation of *A. viridans* var *homari*. The vaccinated lobsters were only able to resist challenges of 200 bacteria/kg of body weight and the resistance induced by this vaccine did not appear until approximately four days post vaccination and declined to minimum levels by 12 days post vaccination.

The vaccine of the present invention has induced a high degree of resistance against much higher challenge doses of bacteria, i.e. 10,000,000 bacteria/kg of body wt. Furthermore, the vaccinated lobsters were still highly resistant against infection at 34 days post vaccination. This is important since there is approximately a two month period in October and November during the usual five months of pounding (from October to February) when resistance to gaffkemia is crucial in preventing an epidemic within the pound.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

EXAMPLE 1

A virulent strain of *Aerococcus viridans* (var. *homari*) was grown in trypticase soy broth (TSB) at 28° C. through three serial transfers to obtain good logarithmic growth. At this point, 0.1 ml of the culture was transferred to 50 ml of TSB containing 10% crab serum. After 6 to 7 hours of growth at 28° C., vancomycin HCl was added to give a concentration of 2 mcg/ml and incubation was continued for 24 more hours. After incubation was complete, cells and other particulate material were collected by centrifugation at 10,000 rpm for 15 minutes, the supernatent removed, filtered through a 0.45 micron sterilizing filter and saved for recombination with the cells. The cells were washed two times with sterile distilled $H_2O$ and suspended in 15 ml of sterile distilled $H_2O$ after the second wash.

Sterilization of the cells was accomplished using short wave U.V. light. 7.5 ml of the cell suspension was placed in a sterile petri dish and exposed to shortwave ultra violet light for 5 minutes at a distance of 3 inches from the source with constant agitation during the 5 minute period. The same procedure was used on the remaining 7.5 ml of suspension. The sterilized suspensions of bacteria were combined in a sterile centrifuge tube and the cells collected by centrifugation at 10,000 rpm for 15 minutes. The supernatant was poured off and the cells suspended in 30 ml of the filtered supernatent previously collected. This suspension was then placed in a sterile vaccine bottle and stored refrigerated. A 2 ml aliquot was taken and tested for sterility by incubation in TSB at 28° C. for 48 hours.

EXAMPLE 2

Two trials have been run with the vaccine of Example 1. The results from the first were the following:

| No. of Lobsters | Treatment 0.5ml/lobster | Challenge of A. viridans (var.) homari 33 days post treatment | Deaths from Gaffkemia |
| --- | --- | --- | --- |
| 8 | Control | $5.0 \times 10^2$/ml | 8 |
| 8 | Vaccine | $5.0 \times 10^2$/ml | 0 |

Hemolymph from the vaccinated lobsters was examined twenty-one days after the time of challenge and all lobsters were found to be free of bacteria. Seven of the eight control lobsters died within 10 days of the challenge and the eighth died at 18 days. All the controls were found to contain high numbers of *A. viridans* var. *homari* at the time of death.

The second experiment was set up to have 5 control lobsters and 10 vaccinated lobsters; however, due to technical difficulties, ten lobsters were lost before the challenge dose was administered. This left three vaccinated and two control lobsters for the remainder of the experiment.

| No. of Lobsters | Treatment .5ml/lobster | Challenge of A. viridans (var.) homari 34 days post treatment | Deaths from Gaffkemia |
| --- | --- | --- | --- |
| 2 | Control | $1.0 \times 10^4$/ml | 2 |
| 3 | Vaccinated | $1.0 \times 10^4$/ml | 0 |

The three vaccinated lobsters survived pathogen free; the two controls died 10 and 15 days post challenge time.

EXAMPLE 3

Thirty liters of vaccine was produced using the following procedure. An inoculum of *A. viridans* was taken from a TSA Slant (20% serum), placed into 4.0 ml of trypticase soy broth (TSB) and incubated at 37° C. for 24 hours. After this incubation, the cells were grown through 3 additional transfers at 37° C. for incubation periods of 12, 8 and 6 hours respectively. An inoculum of 5.0 ml was then removed from the 6 hour culture and placed into each of 10 flasks containing 3 liters of TSB per flask. This was incubated at 37° C. for 4 hours, after which time cell growth was inhibited by the addition of vancomycin HCl to a final concentration of 2 $\mu$g/ml. Incubation was then continued for an additional 12 hours. After thorough mixing, the contents of the flasks were then dispensed into 1 liter intravenous bottles. These bottles were then sealed and autoclaved for 15 minutes at 121° C. under 15 psi pressure. Sterility was checked by inoculation of 1 ml samples of vaccine into each of three tubes containing 3.5 ml of TSB.

EXAMPLE 4

The vaccine of Example 3 was tested for efficacy in five lobsters. Four additional lobsters were used as controls. The control group received a 0.5 ml injection of TSB containing 2 $\mu$g/ml of vancomycin. The vaccinated group of lobsters received a 0.5 ml injection of the vaccine. After a period of 5 days, each lobster was infected with 0.5 ml of a 3% NaCl solution containing 2.4×10⁴ organisms/ml. The lobsters were held at a temperature of 18.5° C.±1° C.

The results of this trial are summarized in Table 1. Two days after infection with *A. viridans,* one of the vaccinated lobsters died from cannibalism. This lobster has been partially eaten and a blood smear did not reveal the presence of *A. viridans.* Control lobsters were found dead on both day 5 and day 6. Blood smears and cultures revealed the presence of *A. viridans.* Also, on day 6 post infection a 0.5 ml blood sample was removed from each of the two remaining controls and four remaining vaccinated lobsters. This sample was inoculated into TSB and incubated for 48 hours at 28° C. The two remaining control lobsters revealed the presence of *A. viridans* while the four vaccinated lobsters were shown to be free of the pathogen.

Table 1

| No. of Lobsters | Lot #1 Treatment 0.5 ml/ lobster | Gaffkemia Vaccine Trial[a] Deaths from gaffkemia or positive blood culters |
|---|---|---|
| 4 | Control | 4[b] |
| 5 | Vaccinated | 0[c] |

[a]All lobsters were challenged 5 days post treatment with 2.4 × 10⁴ org/ml.
[b]of the four lobsters, one died within 5 days of infection, one within 6 days and the remaining two showed positive blood cultures and died within 18 days of infection.
[c]On day two post-challenge, one of the vaccinated lobsters was cannibalized.

The preceding examples can be repeated with similar success by substituting the generically or specifically described reactants and/or operating conditions of this invention for those specifically used in the examples. From the foregoing description, one skilled in the art to which this invention pertains can easily ascertain the essential characteristics thereof and, without departing from the spirit and scope of the present invention, can make various changes and modifications to adapt it to various usages and conditions.

INDUSTRIAL APPLICABILITY

As can be seen from the present specification and examples, the lobster gaffkemia vaccine of the present invention is industrially useful in preventing the spreading of gaffkemia among lobsters being held for market.

What is claimed is:
1. A method for preparing a vaccine suitable for use in protecting lobsters against gaffkemia, which comprises:
    (a) culturing a logarithmic growth phase of the bacteria *Aerococcus viridans* (var. *homari*) in a suitable growth medium containing sources of assimilable complete nutrients for said bacteria;
    (b) adding a sublethal, replication-inhibiting amount of an antibiotic effective against said bacteria to said culture and incubating the resultant admixture for a period of time sufficient to accumulate antigens therein protective against gaffkemia infections; and
    (c) recovering said protective antigens to form a vaccine containing an immunologically effective amount of said antigens 100% free of said living bacteria and substantially free of in vivo effective amounts of said antibiotic.
2. A method according to claim 1, wherein said strain is virulent and said antibiotic is vancomycin.
3. A method according to claim 2, wherein said growth medium is trypticase soy broth.
4. A method according to claim 1, wherein said growth medium contains a metabolically effective amount of crustacean serum and said culturing is effected for a period of time sufficient to metabolize at least a portion of said serum.
5. A method according to claim 4, wherein said crustacean serum is crab serum.
6. A method according to claim 1, wherein the resultant cells are separated from their supernatant, sterilized and re-combined with said supernatant to form said vaccine.
7. A method according to claim 6, wherein said sterilization is effected by exposure to short-wave ultraviolet radiation.
8. A method according to claim 6, wherein said sterilization is effected by autoclaving.
9. A vaccine prepared according to the method of claim 1.
10. A method for immunizing lobsters against gaffkemia, which comprises administering a safe and immunologically effective amount of the vaccine according to claim 9 to a living lobster susceptible to said disease.

* * * * *